(12) United States Patent
Lewis et al.

(10) Patent No.: US 6,410,505 B1
(45) Date of Patent: Jun. 25, 2002

(54) DIMERIC NON-AZO NAPHTHALIMIDES AND USES FOR THE SAME

(75) Inventors: David E. Lewis, Brookings; Ronald E. Utecht, Volga, both of SD (US); Millard M. Judy; J. Lester Matthews, both of Dallas, TX (US)

(73) Assignee: Microbiomed Corp., Dallas, TX (US)

( * ) Notice: Subject to any disclaimer, the term of this patent is extended or adjusted under 35 U.S.C. 154(b) by 0 days.

(21) Appl. No.: 09/438,306

(22) Filed: Jun. 28, 1999

(51) Int. Cl.$^7$ ............... A61K 31/695; A61K 31/69; A61K 31/675; C07D 471/06; C07F 7/02
(52) U.S. Cl. ............... 514/1; 514/63; 514/64; 514/89; 514/278; 514/296; 546/13; 546/14; 546/23; 546/18; 546/100; 530/350
(58) Field of Search ............... 546/100, 98, 13–14, 546/23, 18; 514/296, 278, 89, 63, 64, 1; 530/350

(56) References Cited

U.S. PATENT DOCUMENTS

5,235,045 A 8/1993 Lewis et al. ............... 534/560

*Primary Examiner*—Alan L. Rotman
(74) *Attorney, Agent, or Firm*—Jackson Walker L.L.P.

(57) ABSTRACT

A class of predominantly hydrophilic 1,8-naphthalimide dyes. The dye contains at least two 1,8-naphthalimide ring systems, joined by a spacer moiety. Each of the 1,8-naphthalimide ring system has a ring nitrogen atom and bears, at the 4 position, an amino nitrogen atom, carrying a hydrogen. The remaining unsatisfied valences, if present, of the ring nitrogen atoms or the amino nitrogen atoms, or all, are occupied by one or more alkyl substituents. Each of the 1,8-naphthalimide ring system is free of an azo substituent and is also free of a nucleofuge. Upon activation by an activating agent in an environment independent of the presence or absence of oxygen, these compounds generate activated species. The activated species can cause structural changes in lipid and any associated proteins and polypeptides, extra- or intra-cellular or transmembrane, leading to polymerization and crosslinking.

9 Claims, 3 Drawing Sheets

DIMERIC NON-AZO NAPHTHALIMIDES AND USES FOR THE SAME

FIELD OF THE INVENTION

The present invention relates to dimeric non-azo naphthalimides, or non-azo bis-(benz[de]isoquinoline-1,3-dione) derivatives, their compositions, their preparations, and their uses. More specifically, the present invention relates to predominantly hydrophilic dimeric non-azo naphthalimides joined by a spacer moiety, their compositions, their preparations, and their uses in tissue welding.

Maintenance of close contact between opposed biological tissue surfaces is necessary for access of cellular and molecular species required for formation of new connective tissue components and is thus critical to tissue healing. Ideally, methods of maintaining close contact between healing tissue surfaces should interfere only minimally with tissue or organ function and only minimally affect the healing process itself.

In numerous surgical procedures mechanical closure, e.g. clamping or suturing with biocompatible materials, suffices for functionally adequate wound closure. However these mechanical methods of approximating and holding together wound surfaces can be contraindicated where they interfere seriously with structure or function or their presence complicates healing and restoration of tissue and organ function. For example, sutures cannot be satisfactorily used to hold together surfaces of small blood vessels with diameters 1–2 mm or less. Sutures actually impinge upon the vessel lumen and the fibrous tissue, which always forms in response to the presence of the suture material, further impinges upon the lumen, compromising blood flow.

As another example, anchoring sutures introduce frequent complications during healing of corneal implants. To perform the implant, a full-thickness, circular portion of central recipient cornea is removed using a trephine. A corresponding section of cornea is cut form the donor eye and inserted in the recipient eye and sutured in place. Sutures are left in place until sufficient healing occurs and structural integrity is restored. Sutures can be removed typically as early as 6 months or up to 2 years later.

Surgical complication can arise from the sutures themselves. First, the suture material can initiate an inflammatory response with resulting pain, irritation, and invitation to invasion by vision-impairing blood vessels. Second, suturing makes a hole in the cornea that allows entry into the cornea of infectious agents (e.g., virus) that are ordinarily kept out by the epithelium. Third, sutures do not apply perfectly even pressure along the circumference of the wound (although running sutures are better in this regard). Consequently, areas of the wound not firmly held together are susceptible to leakage of aqueous humor and epithelial downgrowth (into the incision), both serious complications. Together, the problems of inflammation, irritation, wound gape, leakage, and epithelial downgrowth pose significant clinical problems in post surgical management of corneal transplant and are frequent causes for transplant failure.

Use of sutures in affixing bone joint cartilage is precluded because of their mechanical interference with the smooth mutual sliding of cartilage surfaces important to unimpeded joint motion.

As an alternative to suturing, thermally-setting proteinaceous glues have been used with infra-red emitting laser beams to affix or weld, for example, small blood vessels, intestine, bone, and meniscal cartilage. Although mechanical affixation using this method generally has been satisfactory, tissue damaged thermally during lasing and the proteinaceous glue volume promote the formation of an increased volume of connective tissue which increased healing time and mechanically interfered with tissue function.

Different dyes have been used in classical photodynamic therapy, which superficially resembles the new invention described herein is a technique by which membrane alterations can be made in a living cell by irradiation of a compound or dye incorporated into the membrane of the cell. See, U.S. Pat. Nos. 4,613,322; 4,684,521; 4,649,151; and 4,878,891.

Non-azo naphthalimide dyes that are predominantly hydrophobic have been used to cross-link proteins and tissues. See, Lewis et al., U.S. Pat. No. 5,235,045, the entire content of which is hereby incorporated by reference. There is, however, a need for predominantly hydrophilic compounds to better weld or cross-link proteins and tissues having high proteoglycan or water content, such as meniscal cartilage, articular cartilage, and cornea. A means of affixing tissue surfaces in wound closure which results in requisite mechanical strength during healing, seals against leakage of fluid contents, minimal deformation or occlusion of tissue and tissue lumen, and healing without the formation of large volumes of associated connective tissue is needed.

SUMMARY

According to the present invention, predominantly hydrophilic dimeric non-azo naphthalimide dyes are provided. These dyes are "dimeric" in that they contain at least two 1,8-naphthalimide ring systems, joined by a spacer moiety or group. Each of the 1,8-naphthalimide ring system is free of an azo substituent and is also free of a nucleofuge. Further, the use of these new compounds in welding or cross-linking proteins or tissues are given.

More specifically, the present invention relates to a predominantly hydrophilic dimeric 1,8-naphthalimide compounds, having at least two 1,8-naphthalimide ring systems each having a ring nitrogen atom and each bears, at its 4-position, a heteroatomic electron-releasing group which is being characterized as having a heteroatom directly linked to the 4-position of the ring system and having at least one hydrogen directly attached to the heteroatom, such as amino nitrogen atom. Each of the 1,8-naphthalimide ring systems is free of any azo substituent and is also free of any nucleofuge. The two 1,8-naphthalimide ring systems are joined by a spacer moiety or group. The spacer moiety can join the two ring nitrogen atoms, or the two amino nitrogen atoms, or the ring nitrogen atom from one 1,8:-naphthalimide ring system and the amino nitrogen atom from the other 1,8-naphthalimide ring system. The remaining unsatisfied valences, if presence, of the ring nitrogen atoms or the amino nitrogen atoms, or all, are occupied by one or more alkyl substituents. These new naphthalimide dyes are further characterized as giving activated derivatives or species after being activated by a sufficient amount of activating agent in an environment independent of the presence or absence or oxygen.

These new non-azo 1,8-naphthalimide dyes can be activated in the simultaneous presence of an activating agent and the target tissue or protein.

DETAILED DESCRIPTION OF THE INVENTION

Figure 1:
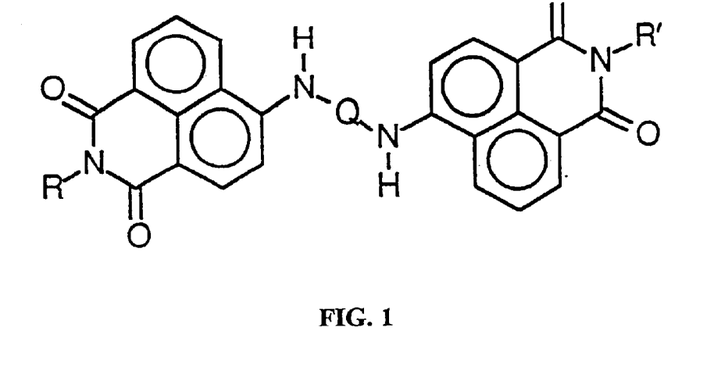
FIG. 1 shows the structural formula of "Type I" dimeric non-azo 1,8-naphthalimide dyes, each having a spacer moiety joining the amino nitrogen atom at the 4-position of the first 1,8-naphthalimide ring system and the amino nitrogen atom at the 4'-position of the second 1,8-naphthalimide ring system.
Figure 2:
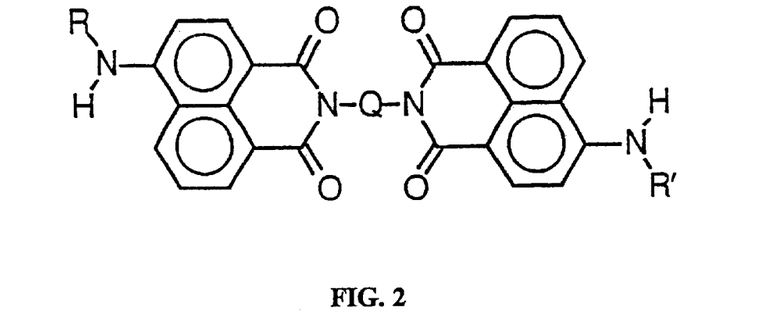
FIG. 2 shows the structural formula of "Type II" dimeric non-azo 1,8-naphthalimide dyes, each having a spacer moiety joining the first ring nitrogen atom of the first 1,8-naphthalimide ring system and the second ring nitrogen atom of the second 1,8-naphthalimide ring system.
Figure 3:
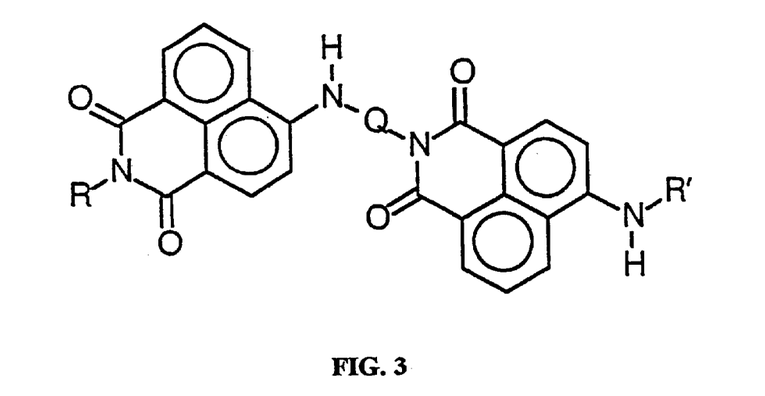
FIG. 3 shows the structural formula of "Type III" dimeric non-azo 1,8-naphthalimide dyes, each having a spacer moiety joining the amino nitrogen at the 4-position of the first 1,8-naphthalimide ring system and the ring nitrogen atom of the second 1,8-naphthalimide ring system.

The generic formula for non-azo 1,8-naphthalimide dyes of the present invention are represented by Types I, II, and III compounds as shown in FIGS. 1, 2, and 3, respectively. The "Q" is the spacer moiety.

Types I, II and III compounds, having mixtures of stereoisomers are compounds wherein:

R and R' are the same or different and are:

a straight-chain or branched chain alkyl, $C_nH_kX_mY_p$ where X is a Group VIA element selected from the group O, S and Se, Y is a Group VA element selected from the group N, P and As (n=2–200, $1 \leq m \leq n$, $1 \leq p \leq n$, 2n<m+p<4n, $1 \leq k \leq 2n+1+p$) and wherein they are free of X—X, X—Y or Y—Y bonds; or monocyclic, polycyclic, fused-ring, bridged ring or spirocyclic alicyclic alkyl $C_nH_{2q+p+1}X_mY_p$ where X is a Group VIA element selected from the group consisting of O, S and Se, Y is a Group VA element selected from the group consisting of N, P and As (n=2–200, q<n, $1 \leq m \leq n$, $1 \leq p \leq n$, 2n<m+p<4n, $1 \leq m \leq n$) with saturated or unsaturated side-chains, branched or unbranched, and wherein they are free of X—X, X—Y or Y—Y bonds; or a straight-chain or branched chain alkyl, $C_nH_kX_mY_p$ where X is a is a Group VIA element selected from the group consisting of O, S and Se, Y is a Group VA element selected from the group consisting of N, P and As, Ar is an aryl group derived from an aromatic compound selected from the group consisting of benzene, pyridine, furan, pyrrole, thiophene, indole, imidazole, oxazole, isozazole, thiazole, benzofuran, benzothiophene, benzimidazole, quinoline, isoquinoline, naphthalene, anthracene, acridine, phenanthrene and their alkylated, halogenated, nitrated or sulfonated derivatives (n=2–200, $1 \leq m \leq n$, $1 \leq p \leq n$, 2n<m+p<4n, $1 \leq r \leq 20$, $1 \leq k \leq 2n+1+p-r$) and wherein they are free of X—X, X—Y or Y—Y bonds; or a straight-chain or branched chain alkyl, $C_nH_kX_mY_pA_a$ where X is a Group VIA element selected from the group consisting of O, S and Se, Y is a Group VA element selected from the group consisting of N, P and As, A is a substituent selected from the group consisting of F, Cl, Br, I, $SiZ_3$, $BZ_2$ or $AlZ_2$, Z is selected from the group consisting of F, Cl, Br, I, OH, $OC_5H_{2t+1}$ (n=2–200, $1 \leq m \leq n$, $1 \leq p \leq n$, 2n<m+p<4n, $1 \leq a \leq 2n$, $1 \leq s \leq 20$, $1 \leq t \leq s$, $1 \leq k \leq 2n+1+p-a$) and wherein they are free of X—X, X—Y or Y—Y bonds; or a straight-chain or branched chain alkyl, $C_nH_kX_mY_pB_b$ where X is a Group VIA element selected from the group consisting of O, S and Se, Y is a Group VA element selected from the group consisting of N, P and As, A is a poly(α-aminoacid) containing up to 300 residues, (n=2–200, $1 \leq m \leq n$, $1 \leq p \leq n$, 2n<m+p<4n, $1 \leq b \leq 20$, $1 \leq s \leq 20$, $1 \leq t \leq s$, $1 \leq k \leq 2n+1+p-b$) and wherein they are free of X—X, X—Y or Y—Y bonds;

Q is:

a straight-chain or branched chain alkyl, $C_nH_kX_mY_p$ where X is a Group VIA element selected from the group consisting of O, S and Se, Y is a Group VA element selected from the group consisting of N, P and As (n=2–200, $1 \leq m \leq n$, $1 \leq p \leq n$, 2n<m+p<4n, $1 \leq k \leq 2n+p$) and wherein they are free of X—X, X—Y or Y—Y bonds; or monocyclic, polycyclic, fused-ring, bridged ring or spirocyclic alicyclic alkyl $C_nH_{2q+p}X_mY_p$ where X is a Group VIA element selected from the group consisting of O, S and Se, Y is a Group VA element selected from the group consisting of N, P and As (n=2–200, q<n, $1 \leq m \leq n$, $1 \leq p \leq n$, 2n<m+p<4n, $1 \leq m \leq n$) with saturated or unsaturated side-chains, branched or unbranched, and wherein they are free of X—X, X—Y or Y—Y bonds; or a straight-chain or branched chain alkyl, $C_nH_kX_mY_pAr_r$ where X is a Group VIA element selected from the group consisting of O,S and Se, Y is a Group VA element selected from the group consisting of N, P and As, Ar is an aryl group derived from an aromatic compound selected from the group consisting of benzene, pyridine, furan, pyrrole, thiophene, indole, imidazole, oxazole, isozazole, thiazole, benzofuran, benzothiophene, benzimidazole, quinoline, isoquinoline, naphthalene, anthracene, acridine, phenanthrene and their alkylated, halogenated, nitrated or sulfonated derivatives (n=2–200, $1 \leq m \leq n$, $1 \leq p \leq n$, 2n<m+p<4n, $1 \leq r \leq 20$, $1 \leq k \leq 2n+p-r$) and wherein they are free of X—X, X—Y or Y—Y bonds; or a straight-chain or branched chain alkyl, $C_nH_kX_mY_pA_a$ where X is a Group VIA element selected from the group consisting of O,S and Se, Y is a Group VA element selected from the group consisting of N, P and As, A is a substituent selected from the group consisting of F, Cl, Br, I, $SiZ_3$, $BZ_2$ or $AlZ_2$, Z is selected from the group consisting of F, Cl, Br, I, OH, $OC_5H_{2t+1}$(n=2–200, $1 \leq m \leq n$, $1 \leq p \leq n$, 2n<m+p<4n, $1 \leq a \leq 2n$, $1 \leq s \leq 20$, $1t \leq s$, $1 \leq k \leq 2n+p-a$)and wherein they are free of X—X, X—Y or Y—Y bonds; or a straight-chain or branched chain alkyl, $C_nH_kX_mY_pB_b$ where X is a Group VIA element selected from the group consisting of O, S and Se, Y is a Group VA element selected from the group consisting of N, P and As, B is a poly(α-aminoacid) containing up to 300 residues, (n=2–200, $1 \leq m \leq n$, $1 \leq p \leq n$, 2n<m+p<4n, $1 \leq b \leq 20$, $1 \leq s \leq 20$, $1 \leq t \leq s$, $1 \leq k \leq 2n+p-b$) and wherein they are free of X—X, X—Y or Y—Y bonds; or pharmaceutically acceptable salts thereof.

As used herein, the words "dye" is interchangeable with the word "compound," as referred to non-azo 1,8-naphthalimides.

A "non-azo compound" or dye is one that does not possess a functional grouping having two nitrogen atoms connected by a double bond.

A nucleofuge is any group which can be displaced from a molecule by a nucleophile. Examples of nucleofuge includes halogens, sulfonate esters, quaternary ammonium salts.

As used herein, the words "unsatisfied valences" mean less than tervalent. Thus, any nitrogen atom which is less than tervalent or tri-coordinate contains unsatisfied valences.

The "activating agent" as used herein denotes a means or an agent that is capable of activating, exciting, or sensitizing a photoactive compound. The activating agent can be radiated energy, electromagnetic energy, laser, electric current, electrons, thermal neutrons or chemicals. The electromagnetic spectrum can include visible light, xenon light, laser light, near infrared and ultraviolet light. The laser or other radiation energy can be continuous or pulsed. The pulsed energy used is such that the energy supplied has a multiple number of short pulses of relatively high energy, but at the same time, has a much lower average energy rate. The laser could be a Helium-Cadmium laser, argon ion laser, a solid state laser, a gas discharge laser, krypton laser, argon ion pumped dye laser, or hollow cathode metal vapor laser or semiconductor diode laser, and others. Even sources such as conventional filament lamp source with appropriate filtering, an arc lamp source with appropriate filtering, even a pulsed xenon flash lamp with appropriate filtering could be used, or light emitting semiconductor such as GaN and ZnSe diodes.

The term "body tissue" as used herein is to be understood to include "body fluid," red blood cells, white blood cells, platelets, cryo precipitate from blood plasma, other plasma proteins, bone marrow, skin, blood vessel wall, nerve sheath, meniscal cartilage, fermoral articular cartilage, cornea, ligament, tendon and other tissues from an animal or a human.

The term "animal" as used herein is to denote any animal; this includes human and other domestic and farm animals.

The term "carrier" as used herein denotes a vehicle, a solution containing water, buffers, serum, serum proteins, lipoproteins, artificial bio-membranes, micelles, liposomes, monoclonal antibodies, carbohydrates, cyclodextrans, organic solvents or other pharmaceutically acceptable, or compatible, solutions. The carrier, or vehicle, used is pharmaceutically compatible in that it is relatively non-toxic to the normal cells and normal tissues and it does not react with the solute or therapeutic agent contained therein.

The phrase "effective amount" as used herein is to denote the concentration or level of the compound that can attain a particular end, such as cross-linking, without producing pronounced toxic symptoms.

In general, liphophilic 1,8-naphthalimide dyes are readily incorporated into lipid bilayers, membranes and micelles of natural or synthetic origin. Due to the sequestration of these lipophilic dyes into the surface regions of proteins, both cellular and liposomal membranes, and tissues having a high density of biomolecular nucleophilic groups, the covalent reactions initiated by the activated form of these dyes can result in chemical alteration of amino acid residues, of protein and peptide conformation and function, and can cross-link the amino acid residues, peptides, and proteins. Thus, this class of dyes can be used to link desired molecular and biomolecular species to peptides, proteins, cells, and biological tissues as well as other substrates containing nucleophilic groups, and to cross-link peptides, proteins, tissues, and other substrates containing nucleophilic groups selectively upon application of an activating agent, such as electromagnetic radiation with wavelength corresponding in absorption spectrum of the dye absorption spectrum. See, U.S. Pat. No. 5,235,045.

The appropriate electromagnetic radiation absorption spectrum includes the ultraviolet through visible light to near infrared and the K-alpha, etc., X-ray absorption energies of the molecular halogen substituent. Other activating agents include thermal neutrons which could be used to activate boron-containing 1,8-naphthalimide dyes.

The partitioning of non-azo 1,8-naphthalimide dyes into hydrophobic or hydrophilic regions of a tissue, and the capability of activating covalent chemical reactions with nucleophilic amino acid residues allows cross-linking of peptides or proteins located either extra- or intra-cellularly or associated with the bilayer membrane selectively upon exposure to light. No cross-linking occurs until the dye is being activated by an activating agent, such as light. This is in contrast to the use of conventional dark-acting chemical cross-linking or linking agents such as formaldehyde, gluteraldehyde, succinimidyl esters, iodoactamides, or maleimides which act immediately upon contact with the appropriate protein residues during mixing by physical agitation or diffusion.

Thus, with the use of conventional dark-acting agents, it is difficult to delay initiation of the cross-linking chemical reaction until a chosen time during appropriate mixing or sequestration of mixture components. The use of the light activatable 1,8-naphthalimide dyes allows temporary delay of cross-linking until desired mixing or sequestration of liposomal membrane constituents and internalized components has been accomplished. This capability allows, for example, synthesis of liposomes containing a completely cross-linked network of Gramacidin-D peptide units within the lipid bilayer and which contain a peptide or protein or other molecular species within the interior such as hemoglobin. The structural and functional integrity of these molecules has been maintained during the cross-linking process because the lipophilic cross-linking dye is physically isolated from the hydrophilic interior and incapable of chemical reaction with the internalized molecular species. Additionally, the lack of cross-linking in the dark by 1,8-naphthalimide dyes allows greater facility of mixing of the constituent in the dark without fear of reaction.

The newly synthesized class of light-activated protein cross-linking bifunctional naphthalimide dyes offer the possibility of an entirely new approach to hydrophilic tissue bonding that overcomes present difficulties with sutures, thermal welding and exogenous glues. This class of compounds is typified structurally by two photochemically active naphthalimide ring systems linked together by an inert chain, and each ring is also substituted with an inert ligand chain. These "dimeric" naphthalimides absorb light in the range of from about 350 nm to about 550 nm. Preferably, they absorb in the 410–480 nm range of the visible light spectrum with maximum absorption (E about 13,000 l/mole cm) at about 430 nm. Following light absorption, the excited molecule can lose energy either by fluorescent emission or through photochemical reaction and covalent bond formation with an available reactive substrate. Incorporation of polyether chains and charged amino groups render these dyes polar and hydrophilic.

The water solubility of the new class of naphthalimide dyes and their ability to penetrate various biological tissues depends strongly upon their molecular structure. Tissues such as cornea, meniscus and articular cartilage tend to exclude hydrophilic forms of dyes. This probably stems from the highly polar and ionically charged nature of proteoglycans and other structural molecules present in high concentrations in these tissues. The hydrophilic nature of the molecular environment of these tissues would exclude the close positioning of the hydrophobic dye required for photochemical linking, necessary for welding two opposing surfaces.

The dyes of the present invention are hydrophilic and most are soluble in water and other polar solvents. They readily associate with and penetrate the surface of tissues, such as, corneal stroma, meniscus and articular cartilage upon exposure to solution.

Light induced covalent linking of the non-azo 1,8-naphthalimide dyes with a substrate also allows their use in linking a desired biomolecular or pharmaceutical agent to target biological cells or to the surface of a biological tissue at a desired time.

Use of light activation of these dyes also allows cross-linking of proteins at different tissue surfaces in order to bond or weld biological tissues together and avoid unwanted intermediate reaction. The advantage of light induced tissue welding over thermally induced welding is less damage to tissue adjacent to the welded area due to lack of heating of surrounding tissues by diffusion during the procedure.

Chemical Syntheses

Given below are different general synthetic methods that can be used for the syntheses of the new non-azo 1,8-naphthalimide dyes. The synthetic methods are Methods A-H given below:

A. 4-Chloro-N-alkyl-1,8-naphthalimides may be prepared as adapted from Lewis, et al., U.S. Pat. No. 5,235,045 (Aug. 10, 1993). A typical procedure is as follows:

To a suspension or solution of freshly-recrystallized 4-chloro-1,8-naphthalic anhydride (1 eq.) in a solvent (acetic acid or ethanol; 10-15 mL per gram of anhydride) is added the amine R—$NH_2$ or R'—$NH_2$ (2 eq.). The solution is heated under reflux for 16–18 hours, after which the mixture is poured into water (approximately 5 mL of water per mL of solution). The solid which precipitates is collected by vacuum filtration and washed with water and ethanol. The material is sufficiently pure for conversion directly to the 4-aminonaphthalimide; it may be further purified by recrystallization from acetic acid.

B. 2-{ω'-[6"-chloro-(1"H)benz[de]isoquinolin-1",3"(2"H)-dion-2"-yl ]-1'-alkyl}-6-chloro-( 1H)benz[de]isoquinolin-1,3(2H)-dione[N,N'-alkylene-bis-(4-chloro-1,8-naphthalimide].

To a solution of freshly-recrystallized 4-chloro-1,8-naphthalic anhydride (2 eq.) in acetic acid (10–15 mL per gram of anhydride) is added the diamine $H_2N$—Q—$NH_2$, (1 eq.). The solution is stirred at 120° C. for 16–18 hours, after which the solution is poured into water (approximately 5 mL water per mL of solution). The precipitated solid is collected by vacuum filtration and washed with water or ethanol. The material is sufficiently pure for conversion directly to the 4-aminonaphthalimide; it may be further purified by recrystallization from acetic acid.

C. Water-insoluble 2-{ω'-[6"-alkylamino-(1"H)benz[de]isoquinolin-1",3"(2"H)-dion-2"-yl]-1'-alkyl }-6-alkylamino-( 1H)benz[de]isoquinolin-1,3(2H)-diones.

The N,N'-alkylene-bis-4-chloro-1,8-naphthalimide (1 eq.) is heated with an excess of the primary amine, R—$NH_2$ or R'—$NH_2$ (usually 5 mL of the amine per gram of chloroimide) at a temperature below 130° C. for 16–18 hours. After this time the solution is poured into water, and the solid precipitated is collected by vacuum filtration. The crude product is purified by recrystallization from acetic acid.

D. Water-soluble 2-{ω'-[6"-alkylamino-(1"H)benz[de]isoquinolin-1",3"(2"H)-dion-2"-yl]- 1'-alkyl }-6-alkylamino-(1H)benz[de]isoquinolin-1,3(2H)-diones.

The N,N'-alkylene-bis-(4-chloro-1,8-naphthalimide (1 eq.) is heated with an excess of the primary amine R—$NH_2$ or R'—$NH_2$, (usually 5 mL of the amine per gram of chloroimide) at a temperature below 130° C. for 16–18 hours. After this time the solution is poured into ethanol, and the solid precipitated is collected by vacuum filtration. The crude product is purified by recrystallization from ethanol.

E. One-Pot Method for Water-soluble 2-{ω'-[6"-alkylamino-(1"H)benz[de]isoquinolin-1",3"(2"H)-dion-2"-yl]-1'-alkyl}-6alkylamino-(1H)benz[de]isoquinolin-1,3 (2H)-diones.

Freshly recrystallized 4-chloro-1,8-naphthalic anhydride (1 eq.) is heated with an excess of the primary amine R—$NH_2$ or R'—$NH_2$, (usually 5 mL of the amine per gram of chloroimide) at a temperature below 130° C. for 16–18 hours. After this time the solution is poured into ethanol, and the solid precipitated is collected by vacuum filtration. The crude product is purified by recrystallization from ethanol.

F. One-Pot Method for 2-{ω'-[6"-alkylamino-(1"H)benz[de]isoquinolin-1",3"(2"H)-dion-2"-yl]-1'-alkyl}-6-alkyl-(1H)benz[de]isoquinolin-1,3(2H)-diones.

The 4-chloro-N-alkyl-1,8-naphthalimide is heated with an excess of the primary amine R'-$NH_2$, (usually 10 mL of the amine per gram of chloroimide) at a temperature below 130° C. for 20–25 hours. After this time the solution is poured into water or ethanol, and the solid precipitated is collected by vacuum filtration. The crude product is purified by recrystallization from ethanol.

G. N,N'-bis-{[2"-alkyl-(1"H)benz[de]isoquinolin-1",3"(2"H)-dion-6"-yl]alkyl}alkane-diamides.

A 2-alkyl-6-(ω'-aminoalkyl)amino-(1H)benz[de] isoquinolin-1,3(2H)-dione (2 eq.) is dissolved in dichloromethane (≈10 mL per gram of imide) and pyridine (2 eq.) and an alkanedioyl chloride (1 eq) are added in sequence. The reaction mixture is allowed to stand at ambient temperature for 24 h, after which time t.l.c. analysis indicates that all the starting material has been consumed. The solvent is evaporated under reduced pressure to affords the crude product as a red-orange oil which is recrystallized from 1-butanol or acetic acid.

H. 6-{ω'-[6"-alkylamino-(1"H)benz[de]isoquinolin-1",3" (2"H)-dion-2"-yl]-1'-alkyl}amino-2-alkyl-(1H)benz[de] isoquinolin-1,3(2H)-diones.

The 2-alkyl-6-(ω'-aminoalkyl)amino-(1H)benz[de] isoquinolin-1,3(2H)-dione (1 eq.) is heated in ethanol or acetic acid (≈10 mL per gram of imide) with freshly recrystallized 4-chloro-1,8-naphthalic anhydride (1 eq.) for 18–24 h. After this time, the solution is poured into water and the solid precipitated is collected by vacuum filtration. The crude product is heated under reflux for 24 h with an excess of 1-butylamine (usually 10 mL per gram of crude bisimide). After this time, the reaction mixture is poured into ethanol, and the crude product is collected by vacuum filtration. The product is purified by recrystallization from ethanol or acetic acid.

Generally, Type I compounds can be prepared by, first, using Method A, followed by Method F. Alternatively, Type I compounds can be prepared by, using Method A, followed by Method C, and, lastly, followed by Method G.

Type II compounds can generally be synthesized by, first, using Method B, followed by Method C. Alternatively, Type II compounds can be synthesized by, first, using Method B, followed by Method D. Still another alternate method to synthesize Type II compound is to use the "one-pot" Method E.

As for Type III compounds, the sequence to use is, first, Method A, followed by Method H.

The following compounds have been prepared by these Methods:

| MONOMERIC NAPHTHALIMIDES USED AS INTERMEDIATES: | | | | |
|---|---|---|---|---|
| R | R' | METHOD | MP | YIELD |
| Cl | $C_6H_{13}$ | A | 168–9 | 65% |
| Cl | $C_4H_9$ | A | 176–8 | 53% |
| Cl | $CH_2COOH$ | A | 222–7 | 80% |
| Cl | $CH_2COOC_2H_5$ | A | 133–6 | 27% |
| Cl | $(CH_2)_2OH$ | A | 187–9 | 89% |
| Cl | $(CH_2)_2OCOCH_3$ | A | 100–3 | 88% |
| $C_8H_{13}$ | $C_6H_{13}$ | E | 59–60 | 65% |
| $(CH_2)_2NH_2$ | $C_6H_{13}$ | F | 59–60 | 65% |
| $(CH_2)_6NH_2$ | $C_6H_{13}$ | F | 152–4 | 85% |
| $CH_2(CH_2OCH_2)_2CH_2NH_2$ | $C_4H_9$ | F | 96–9 | 70% |
| $(CH_2)_2OH$ | $C_6H_{13}$ | F | 123–5 | 66% |
| $CH_2(CH_2OCH_2)_2CH_2NH_2$ | $CH_2COOH$ | F | 219–22 | 79% |
| $C_4H_9$ | $CH_2COOH$ | F | 192–6 | 41% |
| $C_4H_9$ | $(CH_2)_2OCOCH(Br)CH_3$ | F | 255–60 | 83% |
| $(CH_2)_2OH$ | $CH_2COOH$ | F | 202–6 | 31% |
| $C_4H_9$ | $(CH_2)_2OH$ | F | 160–2 | 95% |

| DIMERIC NAPHTHALIMIDE INTERMEDIATES | | | | |
|---|---|---|---|---|
| R=R' | Q | METHOD | MP | YIELD |
| Cl | $CH_3(CH_2OCH_2)_3CH_2$ | 8 | 110–2 | 74% |
| Cl | $CH_2(CH_2OCH_2)_2CH_2$ | 8 | 185–7 | 62% |

| REPRESENTATIVE DIMERIC NAPHTHALIMIDES | | | | | |
|---|---|---|---|---|---|
| Type | R=R' | Q | METHOD | MP | YIELD |
| II | $C_6H_{13}$ | $CH_2(CH_2OCH_2)_2CH_2$ | C | 121–3 | 41% |
| II | $CH_2(CH_2OCH_2)_2CH_2NH_2$ | $CH_2(CH_2OCH_2)_2CH_2$ | E | 156–60 | 23% |
| II | $CH_2(CH_2OCH_2)_3CH_2NH_2$ | $CH_2(CH_2OCH_2)_3CH$ | E | 96–8 | 18% |
| I | $C_4H_9$ | $[CH_2(CH_2OCH_2)_2CH_2NHCO(CH_2)_2]_2$ | G | 67–69 | 67% |
| III | $C_4H_9$ | $CH_2CONH(CH_2CH_2O)CH_2CH_2$ | H | Crude | |
| III | $C_6H_{13}$ | $CH_2CH_2$ | H | Crude | |

Biological Evaluation

1. Methods

The methods of photochemical bonding and determination of tissue bond shear strength are as follows. Briefly, one surface of each of two tissue samples was painted with a solution of a Type II compound wherein R and R' is $-[(CH_2)_2O]_3(CH_2)_2NH_2$ and wherein Q is $-(CH_2)_2-O-(CH_2)_2-O-(CH_2)_2-$ (concentrations 6–16 mM) (see FIG. 2) and the painted surfaces opposed to give an overlapped region of about 0.3×0.3 cm in area and approximately one-third of the length of the rectangular tissue sample. The overlapped strips were carefully wrapped in Mylar film to minimize subsequent water evaporation and clamped between two Pyrex microscope slides with a pressure of approximately 1.6 kg/cm$^2$. The samples were then individually exposed to 457.9 nm light from an Argon ion laser at 250 mW/cm$^2$ irradiance (1 cm diameter beam) for preselected exposure durations. Following light exposure, the bonded sample was axially loaded in tension using discrete weights to determine bond tearing (ultimate shear) strength. Values of bond shear strength were calculated as the ratio of applied force (kg) and overlapped tissue area (cm$^2$) and plotted as a function of light radiant exposure (J/cm$^2$) for each dye concentration (see FIGS. 4 and 5). Each data point is the result obtained for one sample with error bars computed using error propagation theory from uncertainties in applied load (±0.0025 kg) and in the measured dimensions of the overlapped area (±0.01 cm).

Dye concentrations and exposure duration were systematically varied to determine their effects on tissue bond shear strength for (a) porcine cornea (split and reopposed internal surfaces of the stroma), (b) human meniscal cartilage (adjacent sheets cut parallel to the tibial surface and reopposed), and (c) human femoral articular cartilage (adjacent sheets cut approximately parallel to articular surface and reopposed).

2. Tissue Bonding Results

Figure 4:
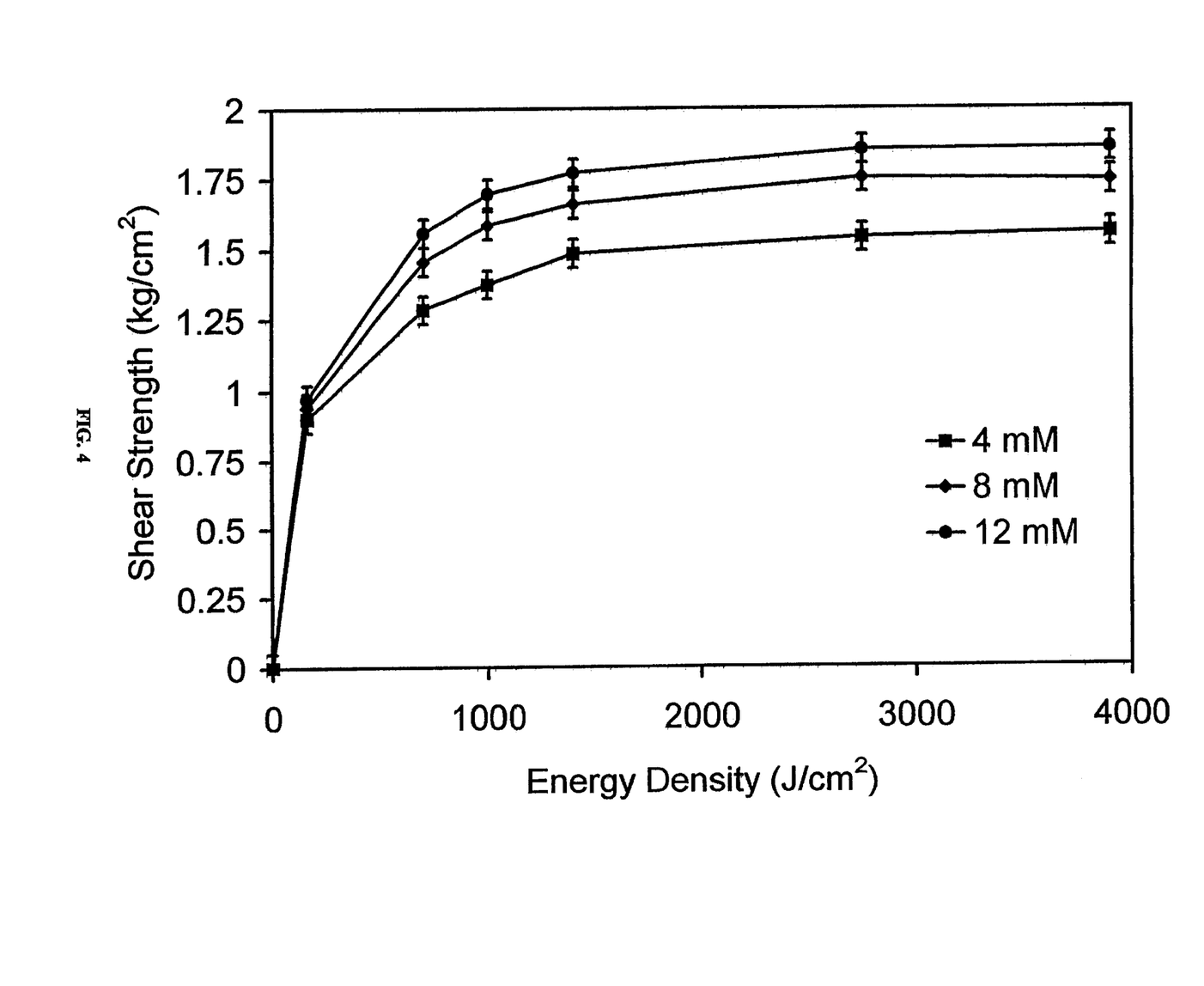
FIG. 4 shows the plot of shear strength vs. energy density in human meniscus cartilage (Parallel)

Human Meniscal Cartilage. As shown in FIG. 4, the shear strength of the photochemical weld in meniscus increased with light exposure and asymptotically approached a limiting value of light exposure for each dye concentration studied. The limiting shear strength value increased with increasing concentration of dye. Shear strengths exceeding 1.3 kg/cm$^2$ were obtained with blue light exposures (457.9 nm) of 1031 J/cm$^2$ and a dye concentration of 4 mM; greater shear strengths were achieved with 8 mM and higher dye concentrations. Optical and electron microscopic examination of the welded region of meniscus disclosed intimate contact and sealing of the two bonded sheets.

Figure 5:
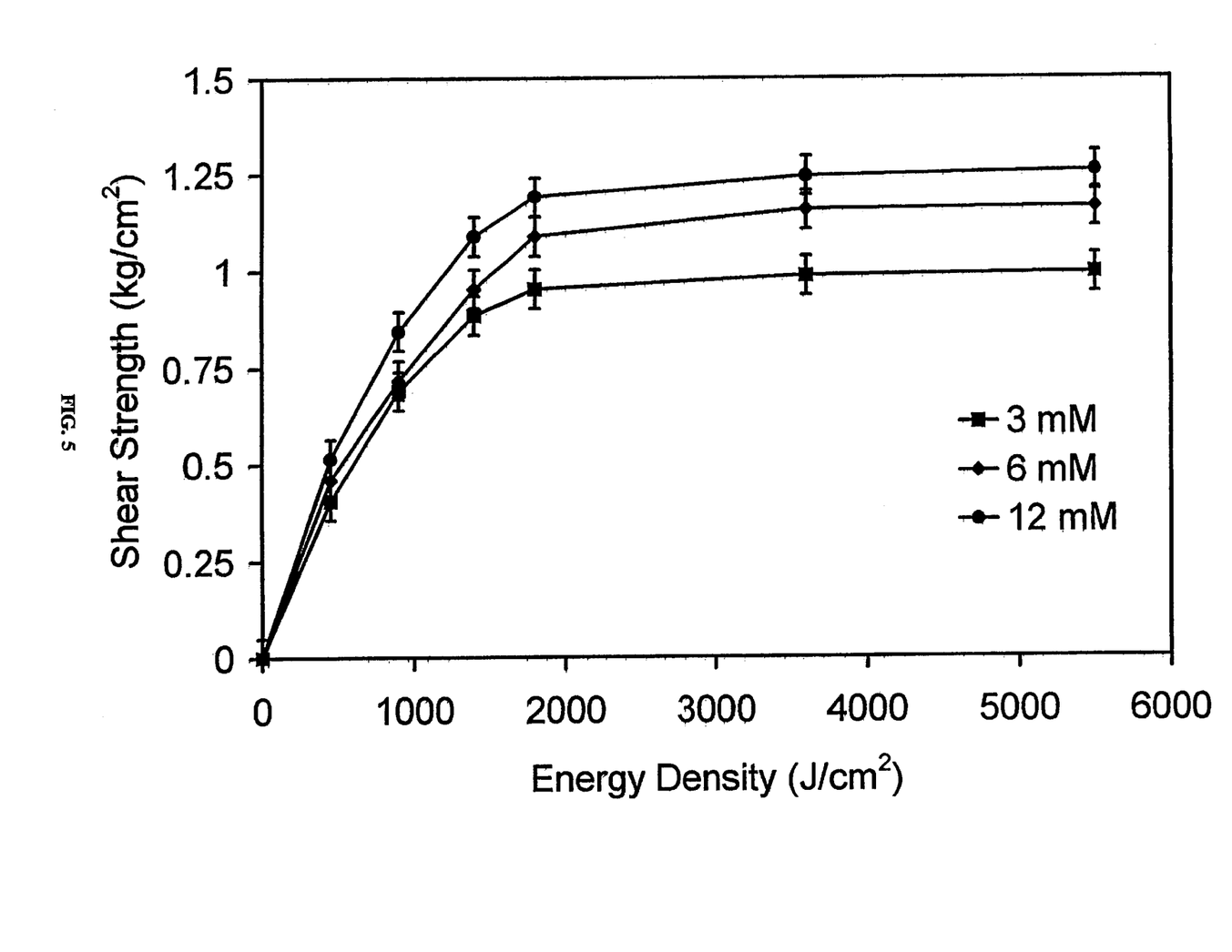
FIG. 5 shows the plot of shear strength vs. energy density in human femoral articular cartilage.

Human Fermoral Articular Cartilage. As shown in FIG. 5, the bond shear strength behavior of photochemically welded articular cartilage sheets with increasing light exposure and dye concentration values are similar to that obtained with human- meniscal cartilage bonds. Ultimate shear strength values, however, were somewhat smaller than values obtained in meniscus, being in the range of approximately 0.8–1.2 kg/cm$^2$.

Porcine Cornea. Strips of porcine cornea, 5 mm wide, were separated along a lamellar plane, parallel to the corneal surface. Hydrophilic dye was applied to the inner (stromal) sides of the tissue and the dye-coated surfaces opposed as described above. Light exposure of 1,031 J/cm$^2$ and dye-solution concentration of 6 mM resulted in a bond shear strength of 0.5±0.1 kg/cm$^2$ in cornea (N=3). This strength is approximately 130 times larger than the calculated 3.81 g/cm$^2$ shell stress in the (assumed spherical) cornea due to the intraocular pressure (22 mm Hg). Thus, photochemical bonding would yield closure of the corneal transplant wound with sufficient strength to prevent leakage of aqueous humour.

3. Summary Results

Bond shear strength values obtained for both meniscal and articular cartilage are significantly greater than values ~0.6 kg/cm$^2$ obtained in the same tissue with transglutaminase glues (K. Jurgensen, et al., "A New Biological Glue for Cartilage-Cartilage Interfaces in Orthopaedic Surgery," presented at the Fourth International Conference on Tissue Transglutaminase and Protein Cross-Linking Reaction, Debrecen, Hungary, Aug. 26–31, 1991) and the value obtained with laser-heated thermal welds in collagenous arterial wall of ~0.3 kg/cm$^2$ (R. D. Jenkins, et al., "Laser Balloon Angioplasty: Effect of Tissue Temperature on Weld Strength of Human Postmortem Intima-Media Separations," Lasers Surg Med 8:30–39, 1988). The entire contents of both of those two references are hereby incorporated by reference.

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto.

What is claimed is:

1. A compound having the formula:

which is a mixture of stereoisomers, wherein:
R and R' are the same or different and are:
a straight-chain or branched chain alkyl, $C_nH_kX_mY_p$ where X is a Group VIA element selected from the group O, S and Se, Y is a Group VA element selected from the group N, P and As (n=2–200, $1 \leq m \leq n$, $1 \leq p \leq n$, $2n < m+p < 4n$, $1 \leq k \leq 2n+1+p$) and wherein they are free of X—X, X—Y or Y—Y bonds; or
monocyclic, polycyclic, fused-ring, bridged ring or spirocyclic alicyclic alkyl $C_nH_{2q+p+1}X_mY_p$ where X is a Group VIA element selected from the group consisting O, S and Se, Y is a Group VA element selected from the group consisting of N, P and As (n=2–200, q<n, $1 \leq m \leq n$, $1 \leq p \leq n$, $2n < m+p < 4n$, $1 \leq m \leq n$) with saturated or unsaturated side-chains, branched or unbranched, and wherein they are free of X—X, X—Y or Y—Y bonds; or
a straight-chain or branched chain alkyl, $C_nH_kX_mY_pAr_r$ where X is a Group VIA element selected from the group consisting O, S and Se, Y is a Group VA element selected from the group consisting of N, P and As, Ar is an aryl group derived from an aromatic compound selected from the group consisting of benzene, pyridine, furan, pyrrole, thiophene, indole, imidazole, oxazole, isozazole, thiazole, benzofuran, benzothiophene, benzimidazole, quinoline, isoquinoline, naphthalene, anthracene, acridine, phenanthrene and their alkylated, halogenated, nitrated or sulfonated derivatives (n=2–200, $1 \leq m \leq n$, $1 \leq p \leq n$, $2n < m+p < 4n$, $1 \leq r \leq 20$, $1 \leq k \leq 2n+1+p-r$) and wherein they are free of X—X, X—Y or Y—Y bonds; or
a straight-chain or branched chain alkyl, $C_nH_kX_mY_pA_a$ where X is a Group VIA element selected from the group consisting of O, S and Se, Y is a Group VA element selected from the group consisting of N, P and As, A is a substituent selected from the group consisting of F, Cl, Br, I, $SiZ_3$, $BZ_2$ or $AlZ_2$, Z is selected from the group consisting of F, Cl, Br, I, OH, $OC_sH_{2t+1}$ (n=2–200, $1 \leq m \leq n$, $1 \leq p \leq n$, $2n < m+p < 4n$, $1 \leq a \leq 2n$, $1 \leq s \leq 20$, $1 \leq t \leq s$, $1 \leq k \leq 2n+1+p-a$) and wherein they are free of X—X, X—Y or Y—Y bonds; or
a straight-chain or branched chain alkyl, $C_nH_kX_mY_pB_b$ where X is a Group VIA element selected from the group consisting O, S and Se, Y is a Group VA element selected from the group consisting of N, P and As, A is a poly(α-aminoacid) containing up to 300 residues, (n=2–200, $1 \leq m \leq n$, $1 \leq p \leq n$, $2n < m+p < 4n$, $1 \leq b \leq 20$, $1 \leq s \leq 20$, $1 \leq t \leq s$, $1 \leq k \leq 2n+1+p-b$) and wherein they are free of X—X, X—Y or Y—Y bonds;

Q is:
a straight-chain or branched chain alkyl, $C_nH_kX_mY_p$ where X is a Group VIA element selected from the group consisting O, S and Se, Y is a Group VA element selected from the group consisting of N, P and As (n=2–200, $1 \leq m \leq n$, $0 \leq p \leq n$, $2n < m+p < 4n$, $1 \leq k \leq 2n+p$) and wherein they are free of X—X, X—Y or Y—Y bonds; or
monocyclic, polycyclic, fused-ring, bridged ring or spirocyclic alicyclic alkyl $C_nH_{2q+p}X_mY_p$ where X is a Group VIA element selected from the group consisting O, S and Se, Y is a Group VA element selected from the group consisting of N, P and As (n=2–200, q<n, $1 \leq m \leq n$, $0 \leq p \leq n$, $2n < m+p < 4n$, $1 \leq m \leq n$) with saturated or unsaturated side-chains, branched or unbranched, and wherein they are free of X—X, X—Y or Y—Y bonds; or
a straight-chain or branched chain alkyl, $C_nH_kX_mY_pAr_r$ where X is a Group VIA element selected from the group consisting O, S and Se, Y is a Group VA element selected from the group consisting of N, P and As, Ar is an aryl group derived from an aromatic compound selected from the group consisting of benzene, pyridine, furan, pyrrole, thiophene, indole, imidazole, oxazole, isozazole, thiazole, benzofuran, benzothiophene, benzimidazole, quinoline, isoquinoline, naphthalene, anthracene, acridine, phenanthrene and their alkylated, halogenated, nitrated or sulfonated derivatives (n=2–200, $1 \leq m \leq n$, $0 \leq p \leq n$, $2n < m+p < 4n$, $1 \leq r \leq 20$, $1 \leq k \leq 2n+p-r$) and wherein they are free of X—X, X—Y or Y—Y bonds; or
a straight-chain or branched chain alkyl, $C_nH_kX_mY_pA_s$ where X is a Group VIA element selected from the group consisting of O, S and Se, Y is a Group VA element selected from the group consisting of N, P and As, A is a substituent selected from the group consisting of F, Cl, Br, I, $SiZ_3$, $BZ_2$ or $AlZ_2$, Z is selected from the group consisting of F, Cl, Br, I, OH, $OC_sH_{2t-1}$ (n=2–200, $1 \leq m \leq n$, $0 \leq p \leq n$, $2n<m+p<4n$, $1 \leq a \leq 2n$, $1 \leq s \leq 20$, $1 \leq t \leq s$, $1 \leq k \leq 2n+p-a$) and wherein they are free of X—X, X—Y or Y—Y bonds; or a straight-chain or branched chain alkyl, $C_nH_kX_mY_pB_b$, where X is a Group VIA element selected from the group consisting O, S and Se, Y is a Group VA element selected from the group consisting of N, P and As, B is a poly(α-aminoacid) containing up to 300 residues, (n=2–200, $1 \leq m \leq n$, $0 \leq p \leq n$, $2n<m+p<4n$, $1 \leq b \leq 20$, $1 \leq s \leq 20$, $1 \leq t \leq s$, $1 \leq k \leq 2n+p-b$) and wherein they are free of X—X, X—Y or Y—Y bonds;

or pharmaceutically acceptable salts thereof.

2. A compound having the formula which is a mixture of stereoisomers, wherein $1 \leq n \leq 20$, and R and R' are the same or different and are:

a straight-chain or branched chain alkyl, $C_mH_k$ ($1 \leq m \leq 20$: $1 \leq k \leq 2m+1$): or a straight-chain or branched chain alkyl, $C_mH_{k+q}O_pN_q$ ($1 \leq m \leq 20$: $1 \leq k \leq 2m+1$: $2 \leq 2p \leq m$: $2m \leq p+q \leq 4m$), wherein they are free of O—O, N—N or N—O bonds;

R" is:

H, $CH_3$, $C_2H_5$, $C_3H_7$, $C_4H_9$, $C_5H_{11}$, $C_6H_{13}$; and

X is:

O, NH, $NCH_3$, $NC_2H_5$;

or pharmaceutically acceptable salts thereof.

3. A composition for cross-linking protein, which comprises an effective amount of the dimeric 1,8 naphthalimide compound according to claim 2, or its derivative, in combination with an acceptable carrier.

4. A method for affixing a dimeric 1,8-naphthalimide compound according to claim 2 or its derivative to a protein, the method comprising:

admixing an effective amount of the dimeric 1,8 naphthalimide according to claim 2 with the protein to give a resultant mixture, and activating the resultant mixture with a sufficient amount of an activating agent to affix the dimeric 1,8 naphthalimide compound according to claim 2 to the protein.

5. A method for cross-linking a first protein to a second protein, the method comprising:

admixing the first protein and the second protein with an effective amount of a dimeric 1,8-naphthalimide compound according to claim 2 or its derivative, to give a resultant mixture;

activating the resultant mixture with a sufficient amount of an activating agent to cross-link the first protein to the second protein.

6. A method of bonding a first body tissue to an adjacent second body tissue, the method comprising:

coating a surface of each of the first and the second body tissues with a sufficient amount of a dimeric 1,8-naphthalimide compound according to claim 2 or its derivative, to give a first coated body tissue and a second coated body tissue;

placing the first coated body tissue and the second coated body tissue in close proximity to give a resultant mixture; and activating the resultant mixture with a sufficient amount of an activating agent to bond the first and the second body tissues.

7. A method claim 6, wherein the first tissue is meniscal cartilage, articular cartilage or cornea.

8. A method claim 6, wherein the second tissue is meniscal cartilage, articular cartilage or cornea.

9. A bonded tissue, comprising at least two tissues, prepared in accordance with the method of claim 6.

* * * * *

UNITED STATES PATENT AND TRADEMARK OFFICE
CERTIFICATE OF CORRECTION

| | | |
|---|---|---|
| PATENT NO. | : 6,410,505 B1 | |
| APPLICATION NO. | : 09/438306 | |
| DATED | : June 25, 2002 | |
| INVENTOR(S) | : David E. Lewis et al. | |

It is certified that error appears in the above-identified patent and that said Letters Patent is hereby corrected as shown below:

Col. 3, line 29, replace "$2n<m+p<4n$" with --$2\leq m+p \leq 2n$--.

Col. 3, line 32, replace "$C_nH_{2q+p+1}X_mY_p$" with --$C_nH_{2n+p+1}X_mY_p$--.

Col. 3, line 36, delete "$q<n$" and replace "$2n<m+p<4n$" with --$2\leq m+p \leq 2n$--.

Col. 3, line 37, delete "$1\leq m \leq n$".

Col. 3, line 40, replace "$C_nH_kX_mY_p$" with --$C_nH_kX_mY_pAr_r$--.

Col. 3, line 52, replace "$2n<m+p<4n$" with --$2\leq m+p \leq 2n$--.

Col. 3, lines 62-63, replace "$2n<m+p<4n$" with --$2\leq m+p \leq 2n$--.

Col. 3, line 63, delete "$1\leq s \leq 20, 1\leq t \leq s$".

Col. 4, line 3, replace "A" with --B--.

Col. 4, lines 4-5, replace "$2n<m+p<4n$" with --$2\leq m+p \leq 2n$--.

Col. 4, line 5, delete "$1\leq s \leq 20, 1\leq t \leq s$".

Col. 4, line 13, replace "$1\leq p \leq n$" with "$0\leq p \leq n$" and replace "$2n<m+p<4n$" with --$2\leq m+p \leq 2n$--.

Col. 4, line 16, replace "$C_nH_{2q+p}X_mY_p$" with --$C_nH_{2n+p}X_mY_p$--.

Col. 4, line 20, delete "$q<n$" and replace "$2n<m+p<4n$" with --$2\leq m+p \leq 2n$--.

Col. 4, line 21, delete "$1\leq m \leq n$".

Col. 4, line 35, replace "$2n<m+p<4n$" with --$2\leq m+p \leq 2n$--.

Col. 4, lines 45-46, replace "$2n<m+p<4n$" with --$2\leq m+p \leq 2n$--.

Col. 4, line 46, delete "$1\leq s \leq 20, 1t \leq s$".

Col. 4, lines 54-55, replace "$2n<m+p<4n$" with --$2\leq m+p \leq 2n$--.

Col. 4, line 55, delete "$1\leq s \leq 20, 1\leq t \leq s$".

Col. 11, line 55, replace "$2n<m+p<4n$" with --$2\leq m+p \leq 2n$--.

Col. 11, line 58, replace "$C_nH_{2q+p+1}X_mY_p$" with --$C_nH_{2n+p+1}X_mY_p$--.

Signed and Sealed this
Thirty-first Day of July, 2012

David J. Kappos
*Director of the United States Patent and Trademark Office*

CERTIFICATE OF CORRECTION (continued)
U.S. Pat. No. 6,410,505 B1

Col. 11, line 59, delete "$1 \leq m \leq n$".

Col. 11, line 62, replace "2n<m+p<4n" with --$2 \leq m+p \leq 2n$--.

Col. 11, line 63, delete "$1 \leq m \leq n$".

Col. 12, lines 21-22, replace "2n<m+p<4n" with --$2 \leq m+p \leq 2n$--.

Col. 12, line 22, delete "$1 \leq s \leq 20, 1 \leq t \leq s$".

Col. 12, line 29, replace "A" with --B--.

Col. 12, lines 30-31, replace "2n<m+p<4n" with --$2 \leq m+p \leq 2n$--.

Col. 12, line 31, delete "$1 \leq s \leq 20, 1 \leq t \leq s$".

Col. 12, line 39, replace "2n<m+p<4n" with --$2 \leq m+p \leq 2n$--.

Col. 12, line 43, replace "$CnH_{2q+p}X_mY_p$" with --$C_nH_{2n+p}X_mY_p$--.

Col. 12, line 47, delete "q<n", replace "2n<m+p<4n" with --$2 \leq m+p \leq 2n$--, and delete second occurrence of "$1 \leq m \leq n$".

Col. 12, line 63, replace "2n<m+p<4n" with --$2 \leq m+p \leq 2n$--.

Col. 12, line 66, replace "$C_nH_kX_mY_pA_s$" with --$C_nH_kX_mY_pA_a$--.

Col. 13, lines 6-7, replace "2n<m+p<4n" with --$2 \leq m+p \leq 2n$--.

Col. 13, line 7, delete "$1 \leq s \leq 20, 1 \leq t \leq s$".

Col. 13, lines 14-15, replace "2n<m+p<4n" with --$2 \leq m+p \leq 2n$--.

Col. 13, line 15, delete "$1 \leq s \leq 20, 1 \leq t \leq s$".